United States Patent
Klug et al.

(10) Patent No.: US 10,961,484 B2
(45) Date of Patent: Mar. 30, 2021

(54) COMPOSITIONS COMPRISING SUGAR AMINE AND FATTY ACID

(71) Applicant: Clariant International Ltd., Muttenz (CH)

(72) Inventors: Peter Klug, Grossostheim (DE); Carsten Cohrs, Frankfurt am Main (DE); Ute Back, Blankenbach (DE); Kevin Mutch, Frankfurt (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 15/766,628

(22) PCT Filed: Oct. 7, 2016

(86) PCT No.: PCT/EP2016/074085
§ 371 (c)(1),
(2) Date: Apr. 6, 2018

(87) PCT Pub. No.: WO2017/060481
PCT Pub. Date: Apr. 13, 2017

(65) Prior Publication Data
US 2018/0282664 A1  Oct. 4, 2018

(30) Foreign Application Priority Data
Oct. 9, 2015 (DE) .................. 10 2015 219 651.8

(51) Int. Cl.
| | | |
|---|---|---|
| C11D 1/04 | (2006.01) |
| C11D 1/14 | (2006.01) |
| C11D 1/29 | (2006.01) |
| C11D 1/66 | (2006.01) |
| C11D 3/22 | (2006.01) |
| A61Q 19/10 | (2006.01) |
| C11D 9/30 | (2006.01) |
| C11D 3/30 | (2006.01) |
| A61K 8/36 | (2006.01) |
| A61K 8/60 | (2006.01) |
| C11D 1/72 | (2006.01) |

(Continued)

(52) U.S. Cl.
CPC .............. *C11D 3/227* (2013.01); *A61K 8/361* (2013.01); *A61K 8/463* (2013.01); *A61K 8/466* (2013.01); *A61K 8/60* (2013.01); *A61Q 19/10* (2013.01); *C11D 1/14* (2013.01); *C11D 1/143* (2013.01); *C11D 1/146* (2013.01); *C11D 1/29* (2013.01); *C11D 1/662* (2013.01); *C11D 1/72* (2013.01); *C11D 1/722* (2013.01); *C11D 3/2079* (2013.01); *C11D 3/22* (2013.01); *C11D 3/221* (2013.01); *C11D 3/30* (2013.01); *C11D 9/30* (2013.01); *C11D 17/08* (2013.01)

(58) Field of Classification Search
CPC .... C11D 1/14; C11D 1/29; C11D 1/72; C11D 1/722; C11D 1/662; C11D 3/22; C11D 3/221; C11D 3/30

USPC ....... 510/127, 136, 137, 138, 238, 356, 357, 510/470, 488, 499, 505
See application file for complete search history.

(56) References Cited

U.S. PATENT DOCUMENTS

| | | |
|---|---|---|
| 2,016,962 A | 10/1935 | Flint |
| 2,667,478 A | 1/1954 | Schwartz |

(Continued)

FOREIGN PATENT DOCUMENTS

| | | |
|---|---|---|
| CA | 2117007 | 9/1994 |
| CA | 1333226 | 11/1994 |

(Continued)

OTHER PUBLICATIONS

"Product Specification: N-octanoyl-N-methylglucamine", Jun. 29, 2000 (Jun. 29, 2000), pp. 1-1, XP055098500, Retrieved from the Internet: URL:http://www.sigmaaldrich.com/Graphics/COfAInfo/SigmaSAPQM/SPEC/03/03129/03129 -BULKSIGMA.pdf.

(Continued)

Primary Examiner — Gregory R Delcotto
(74) Attorney, Agent, or Firm — Tod A. Waldrop

(57) ABSTRACT

What are described are compositions comprising a) one or more sugar amines of the formula (I) in which R1 and R2 are independently H, $CH_3$ or 2-hydroxyethyl and/or one or more corresponding protonated sugar amines with the counterion R—COO— in which R is defined as R from the substances of component b) below, and b) one or more substances selected from the group consisting of fatty acids of the formula R—COOH, fatty acid salts of the formula R—COO-M+ and mixtures thereof, in which R is a linear or branched saturated alkyl radical having 11 to 21 carbon atoms or a linear or branched, mono- or polyunsaturated alkenyl radical having 11 to 21 carbon atoms and M+ is a counterion. The compositions described are very advantageous, for example, for production of liquid washing compositions, and of shower gels, liquid soaps or face cleansers. In addition, the sugar amines are advantageously suitable as neutralizing agents for fatty acids.

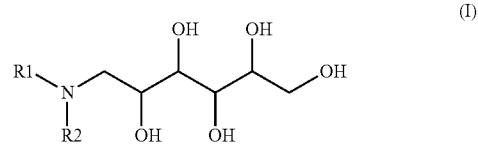

(I)

21 Claims, No Drawings

(51) Int. Cl.
*A61K 8/46* (2006.01)
*C11D 1/722* (2006.01)
*C11D 3/20* (2006.01)
*C11D 17/08* (2006.01)

(56) References Cited

U.S. PATENT DOCUMENTS

| | | |
|---|---|---|
| 2,703,798 A | 3/1955 | Schwartz |
| 2,891,052 A | 6/1959 | Boettner |
| 2,982,737 A | 5/1961 | Boettner |
| 2,993,887 A | 7/1961 | Zech |
| 3,002,923 A | 10/1961 | Barker |
| 3,272,795 A | 9/1966 | Jason |
| 4,079,078 A | 3/1978 | Collins |
| 4,341,559 A | 7/1982 | Friedemann |
| 4,400,196 A | 8/1983 | Albrecht |
| 4,413,087 A | 11/1983 | Bernot |
| 4,481,186 A | 11/1984 | Deckner |
| 4,505,827 A | 3/1985 | Rose |
| 4,565,647 A | 1/1986 | Llenado |
| 4,654,207 A | 3/1987 | Preston |
| 4,681,946 A | 7/1987 | Baur |
| 4,981,684 A | 1/1991 | MacKenzie |
| 5,009,814 A | 4/1991 | Kelkenberg |
| 5,194,639 A | 3/1993 | Connor |
| 5,254,281 A | 10/1993 | Pichardo |
| 5,298,195 A | 3/1994 | Brumbaugh |
| 5,317,047 A | 5/1994 | Sabate |
| 5,354,425 A | 10/1994 | Mackey |
| 5,449,770 A | 9/1995 | Shumate |
| 5,454,982 A | 10/1995 | Murch |
| 5,500,155 A | 3/1996 | Weuthen |
| 5,539,134 A | 7/1996 | Strecker |
| 5,559,078 A | 9/1996 | Garst |
| 5,560,873 A | 10/1996 | Chen |
| 5,625,098 A | 4/1997 | Kao |
| 5,691,299 A | 11/1997 | Fabry |
| 5,711,899 A | 1/1998 | Kawa |
| 5,712,235 A | 1/1998 | Nieendick |
| 5,716,922 A | 2/1998 | Curry |
| 5,750,748 A | 5/1998 | Boutique |
| 5,766,267 A | 6/1998 | Schumacher |
| 5,777,165 A | 7/1998 | Kao |
| 5,789,372 A | 8/1998 | Fabry |
| 5,874,096 A | 2/1999 | Hazen |
| 5,945,389 A | 8/1999 | Richard |
| 6,147,045 A | 11/2000 | Lappas |
| 6,147,124 A | 11/2000 | Ansmann |
| 6,165,955 A | 12/2000 | Chen |
| 6,264,961 B1 | 7/2001 | Ansmann |
| 6,274,126 B1 | 8/2001 | Newell |
| 6,288,023 B1 | 9/2001 | Honda |
| 6,329,331 B1 | 12/2001 | Aronson |
| 6,350,788 B1 | 2/2002 | Herold |
| 6,391,962 B2 | 5/2002 | Zerrer |
| 6,455,001 B1 | 9/2002 | Knappe |
| 6,635,708 B1 | 10/2003 | Papenfuhs |
| 6,727,217 B1 | 4/2004 | Nieendick |
| 6,887,838 B2 | 5/2005 | Dykstra |
| 6,903,057 B1 | 6/2005 | Tsaur |
| 7,056,379 B2 | 6/2006 | Nieendick |
| 7,217,752 B2 | 5/2007 | Schmucker-Castner |
| 7,250,392 B1 | 7/2007 | Leonard |
| 7,297,666 B2 | 11/2007 | Kuepper |
| 7,380,606 B2 | 6/2008 | Pursley |
| 7,407,667 B2 | 8/2008 | Zerrer |
| 7,578,995 B2 | 8/2009 | Frantz |
| 7,776,318 B2 | 8/2010 | Bissey-Beugras |
| 7,820,771 B2 | 10/2010 | Lapra |
| 7,872,036 B2 | 1/2011 | Toriyabe |
| 7,897,543 B2 | 3/2011 | Bretschneider |
| 7,998,911 B1 | 8/2011 | Berger |
| 8,084,452 B2 | 12/2011 | Jeschke |
| 8,178,481 B2 | 5/2012 | Sans |
| 8,220,564 B2 | 7/2012 | Runquist |
| 8,263,538 B2 | 9/2012 | Tsaur |
| 8,324,390 B2 | 12/2012 | Fischer |
| 8,404,855 B2 | 3/2013 | Jeschke |
| 8,536,340 B2 | 9/2013 | Hamamoto |
| 8,637,432 B2 | 1/2014 | Baur |
| 8,729,323 B2 | 5/2014 | Kothandaraman |
| 8,759,255 B2 | 6/2014 | Wacker |
| 8,809,547 B2 | 8/2014 | Bretschneider |
| 8,901,041 B2 | 12/2014 | Frisch |
| 9,187,407 B2 | 11/2015 | Koshti |
| 9,504,636 B2 | 11/2016 | Klug |
| 9,949,909 B2 | 4/2018 | Klug |
| 10,172,774 B2 | 1/2019 | Klug |
| 10,265,253 B2 | 4/2019 | Klug |
| 2001/0023298 A1 | 9/2001 | Weinelt |
| 2001/0056048 A1* | 12/2001 | Bertolosso ............ A61K 8/892 510/122 |
| 2002/0004476 A1 | 1/2002 | Pancheri |
| 2002/0040662 A1 | 4/2002 | Dietz |
| 2002/0065198 A1 | 5/2002 | Highsmith |
| 2002/0168417 A1 | 11/2002 | Blease |
| 2003/0004929 A1 | 1/2003 | Julian |
| 2003/0049292 A1 | 3/2003 | Turowski-Wanke |
| 2003/0069153 A1 | 4/2003 | Jordan |
| 2003/0199403 A1 | 10/2003 | Wells |
| 2004/0086470 A1 | 5/2004 | Nieendick |
| 2005/0037926 A1 | 2/2005 | Zerrer |
| 2005/0037942 A1 | 2/2005 | Otterson |
| 2005/0172859 A1 | 8/2005 | Nieendick |
| 2005/0233935 A1* | 10/2005 | Gunn ............... A61K 8/0295 510/418 |
| 2006/0058205 A1 | 3/2006 | Ainger |
| 2006/0079414 A1 | 4/2006 | Nieendick |
| 2006/0089294 A1* | 4/2006 | Depoot ............... C11D 1/04 510/515 |
| 2006/0100127 A1 | 5/2006 | Meier |
| 2006/0110415 A1 | 5/2006 | Gupta |
| 2006/0110432 A1 | 5/2006 | Luu |
| 2006/0135382 A1 | 6/2006 | Molenda |
| 2006/0142291 A1 | 6/2006 | Beilfuss |
| 2006/0166826 A1 | 7/2006 | Zerrer |
| 2006/0171979 A1 | 8/2006 | Calvo |
| 2007/0054820 A1* | 3/2007 | Harichian ............ A61K 8/345 510/130 |
| 2007/0060489 A1 | 3/2007 | Sun |
| 2007/0110700 A1* | 5/2007 | Wells ............... A61K 8/0295 424/70.21 |
| 2007/0128144 A1 | 6/2007 | Bonastre Gilabert |
| 2007/0190004 A1 | 8/2007 | Bockmuhl |
| 2007/0213226 A1 | 9/2007 | Sieverding |
| 2008/0057014 A1* | 3/2008 | Masuda ............... A61K 8/06 424/64 |
| 2008/0317960 A1 | 12/2008 | Pitt |
| 2009/0023622 A1 | 1/2009 | Leidreiter |
| 2009/0042749 A1 | 2/2009 | Meier |
| 2009/0111847 A1 | 4/2009 | Li |
| 2009/0118152 A1* | 5/2009 | Lam ............... A61K 8/0208 510/120 |
| 2009/0124498 A1 | 5/2009 | Von Deyn |
| 2009/0253612 A1 | 10/2009 | Mushock |
| 2009/0257972 A1 | 10/2009 | Dieker |
| 2010/0051200 A1 | 3/2010 | Mueller |
| 2010/0285077 A1 | 11/2010 | Lintner |
| 2010/0326320 A1 | 12/2010 | Swedo |
| 2011/0002865 A1 | 1/2011 | Fournial |
| 2011/0146536 A1 | 6/2011 | Tomlinson |
| 2011/0150786 A1 | 6/2011 | Desenne |
| 2011/0152150 A1* | 6/2011 | Bernard ............... A61K 8/046 510/136 |
| 2011/0177945 A1 | 7/2011 | Klingelhoefer |
| 2011/0251116 A1 | 10/2011 | Aehle |
| 2011/0263471 A1 | 10/2011 | Barnhart |
| 2012/0009127 A1 | 1/2012 | Dasgupta |
| 2012/0010113 A1 | 1/2012 | Hee |
| 2012/0070388 A1* | 3/2012 | Man ............... A61K 8/068 424/59 |
| 2012/0073817 A1 | 3/2012 | Van Zanten |
| 2012/0094890 A1 | 4/2012 | Anantaneni |

(56) References Cited

U.S. PATENT DOCUMENTS

| | | | |
|---|---|---|---|
| 2012/0172223 | A1 | 7/2012 | Wacker |
| 2012/0244092 | A1 | 9/2012 | Moser |
| 2013/0030197 | A1 | 1/2013 | Harichian |
| 2013/0189212 | A1 | 7/2013 | Jawale |
| 2013/0216491 | A1 | 8/2013 | Ogihara |
| 2014/0096969 | A1 | 4/2014 | Ali |
| 2014/0135245 | A1* | 5/2014 | Annaheim ........... A61K 8/0208 510/137 |
| 2014/0230841 | A1 | 8/2014 | Mathonneau |
| 2014/0255330 | A1* | 9/2014 | Cron ................. A61K 8/42 424/65 |
| 2014/0303389 | A1 | 10/2014 | Crosby |
| 2015/0032003 | A1 | 1/2015 | Cho |
| 2015/0125415 | A1 | 5/2015 | Klug |
| 2015/0126424 | A1 | 5/2015 | Klug |
| 2015/0126616 | A1 | 5/2015 | Klug |
| 2015/0133560 | A1 | 5/2015 | Klug |
| 2015/0140048 | A1 | 5/2015 | Klug |
| 2015/0141466 | A1 | 5/2015 | Klug |
| 2015/0141508 | A1 | 5/2015 | Klug |
| 2015/0150767 | A1 | 6/2015 | Klug |
| 2015/0164755 | A1 | 6/2015 | Klug |
| 2015/0164756 | A1 | 6/2015 | Klug |
| 2015/0282478 | A1 | 10/2015 | Baur |
| 2015/0320037 | A1 | 11/2015 | Wacker |
| 2015/0335550 | A1 | 11/2015 | Koshti |
| 2016/0074310 | A1 | 3/2016 | Klug |
| 2016/0136072 | A1 | 5/2016 | Klug |
| 2016/0143828 | A1 | 5/2016 | Klug |
| 2016/0243014 | A1 | 8/2016 | Dahms |
| 2016/0272666 | A1 | 9/2016 | Klug |
| 2016/0361243 | A1 | 12/2016 | Klug |
| 2017/0000710 | A1 | 1/2017 | Klug |
| 2017/0002297 | A1 | 1/2017 | Klug |
| 2017/0044434 | A1 | 2/2017 | Baur |
| 2017/0055524 | A1 | 3/2017 | Baur |
| 2017/0071199 | A1 | 3/2017 | Baur |
| 2017/0101606 | A1 | 4/2017 | Klug |
| 2017/0218293 | A1 | 8/2017 | Klug |
| 2017/0226349 | A1 | 8/2017 | Kupfer |
| 2017/0265477 | A1 | 9/2017 | Baur |
| 2017/0292062 | A1 | 10/2017 | Wylde |
| 2017/0305838 | A1 | 10/2017 | Appel |
| 2018/0215879 | A1 | 8/2018 | Kupfer |
| 2018/0291208 | A1 | 10/2018 | Kupfer |
| 2019/0076344 | A1 | 3/2019 | Klug |

FOREIGN PATENT DOCUMENTS

| | | |
|---|---|---|
| CA | 2127644 | 1/1995 |
| CN | 1061960 | 6/1992 |
| CN | 1077489 | 10/1993 |
| CN | 1078746 | 11/1993 |
| CN | 1088258 | 6/1994 |
| CN | 1140987 | 1/1997 |
| CN | 1141653 | 1/1997 |
| CN | 1155239 | 7/1997 |
| CN | 1184417 A | 6/1998 |
| CN | 1292641 | 4/2001 |
| CN | 1296524 | 5/2001 |
| CN | 1501772 | 6/2004 |
| CN | 1518408 | 8/2004 |
| CN | 1594518 | 3/2005 |
| CN | 100528887 C | 5/2006 |
| CN | 1997341 | 7/2007 |
| CN | 101056959 A | 10/2007 |
| CN | 102186340 | 9/2011 |
| CN | 102595882 | 7/2012 |
| CN | 103468362 | 12/2013 |
| CN | 103468382 | 12/2013 |
| CN | 104918490 | 9/2015 |
| DE | 1956509 | 5/1971 |
| DE | 2226872 A1 | 12/1973 |
| DE | 4238211 | 1/1994 |
| DE | 4235783 | 4/1994 |
| DE | 4435383 | 11/1995 |
| DE | 19507531 | 9/1996 |
| DE | 19701127 | 7/1998 |
| DE | 19808824 | 10/1999 |
| DE | 19846429 | 4/2000 |
| DE | 19916090 | 10/2000 |
| DE | 10117993 | 10/2002 |
| DE | 10130357 | 1/2003 |
| DE | 102007034438 | 1/2009 |
| DE | 202013011412 | 1/2014 |
| DE | 202013011413 | 1/2014 |
| DE | 102012021647 | 5/2014 |
| EP | 0039860 | 11/1981 |
| EP | 0048436 | 3/1982 |
| EP | 0285768 | 10/1988 |
| EP | 0285786 | 10/1988 |
| EP | 0336151 | 10/1989 |
| EP | 0378985 | 7/1990 |
| EP | 0407874 | 1/1991 |
| EP | 0412849 A2 | 2/1991 |
| EP | 0539588 | 5/1993 |
| EP | 0550637 | 7/1993 |
| EP | 0572723 | 12/1993 |
| EP | 0614881 | 9/1994 |
| EP | 0633244 | 1/1995 |
| EP | 0709449 | 5/1996 |
| EP | 0745719 | 12/1996 |
| EP | 0769548 A1 | 4/1997 |
| EP | 0774503 A1 | 5/1997 |
| EP | 0995994 | 4/2000 |
| EP | 1043017 | 10/2000 |
| EP | 1078978 | 2/2001 |
| EP | 1093722 | 4/2001 |
| EP | 1110944 | 6/2001 |
| EP | 1177223 | 2/2002 |
| EP | 1379129 | 1/2004 |
| EP | 1422288 | 5/2004 |
| EP | 1529832 | 5/2005 |
| EP | 1676831 | 7/2006 |
| EP | 1716842 | 11/2006 |
| JP | S4810053 B | 2/1973 |
| JP | S63270534 | 11/1988 |
| JP | H06501731 | 2/1994 |
| JP | H06501733 | 2/1994 |
| JP | H06240599 | 8/1994 |
| JP | H07507341 | 8/1995 |
| JP | H0812993 | 1/1996 |
| JP | H0848618 | 2/1996 |
| JP | H09502476 | 3/1997 |
| JP | H09506683 | 6/1997 |
| JP | H09510956 | 11/1997 |
| JP | H10501279 | 2/1998 |
| JP | H10508043 | 8/1998 |
| JP | H11505839 | 5/1999 |
| JP | H11246890 | 9/1999 |
| JP | H11512334 | 10/1999 |
| JP | 2000512286 | 9/2000 |
| JP | 2000297028 | 10/2000 |
| JP | 2001501635 | 2/2001 |
| JP | 2001131579 | 5/2001 |
| JP | 2001247528 | 9/2001 |
| JP | 2002542344 A | 12/2002 |
| JP | 2006183030 | 7/2006 |
| JP | 2006183039 | 7/2006 |
| JP | 2007538023 | 12/2007 |
| JP | 2008110953 | 5/2008 |
| JP | 2010018586 | 1/2010 |
| JP | 2010037252 | 2/2010 |
| JP | 2013534232 | 9/2013 |
| JP | 2014532815 | 12/2014 |
| JP | 2015518026 | 6/2015 |
| JP | 2017526776 | 9/2017 |
| WO | 9205764 A1 | 4/1992 |
| WO | 9206073 | 4/1992 |
| WO | 9206154 | 4/1992 |
| WO | 9206158 A1 | 4/1992 |
| WO | 9206161 A1 | 4/1992 |
| WO | 9206162 A1 | 4/1992 |

(56) References Cited

FOREIGN PATENT DOCUMENTS

| | | |
|---|---|---|
| WO | 9318125 | 9/1993 |
| WO | 9319149 | 9/1993 |
| WO | 9410130 | 5/1994 |
| WO | 9412608 | 6/1994 |
| WO | 9412609 | 6/1994 |
| WO | 9419941 | 9/1994 |
| WO | 9516824 | 6/1995 |
| WO | 9517880 A1 | 7/1995 |
| WO | 9519415 | 7/1995 |
| WO | 9523840 | 9/1995 |
| WO | 9533033 | 12/1995 |
| WO | 9533035 | 12/1995 |
| WO | 9603974 A1 | 2/1996 |
| WO | 9610386 | 4/1996 |
| WO | 9614374 | 5/1996 |
| WO | 9616540 | 6/1996 |
| WO | 9628023 | 9/1996 |
| WO | 9637589 | 11/1996 |
| WO | 9637592 | 11/1996 |
| WO | 9747284 A1 | 12/1997 |
| WO | 9800496 A1 | 1/1998 |
| WO | 9841601 | 9/1998 |
| WO | 9856496 | 12/1998 |
| WO | 9951716 | 10/1999 |
| WO | 0065014 | 11/2000 |
| WO | 0137658 | 5/2001 |
| WO | 0160877 | 8/2001 |
| WO | 02089575 | 11/2002 |
| WO | 2002096882 | 12/2002 |
| WO | 03000055 | 1/2003 |
| WO | 2003106457 | 12/2003 |
| WO | 2004056358 | 7/2004 |
| WO | 2004099150 | 11/2004 |
| WO | 2004099160 | 11/2004 |
| WO | 2005035486 | 4/2005 |
| WO | 2005063094 | 7/2005 |
| WO | 2005077934 | 8/2005 |
| WO | 2005117580 | 12/2005 |
| WO | 2006043635 | 4/2006 |
| WO | 2006056433 | 6/2006 |
| WO | 2006089633 | 8/2006 |
| WO | 2006100288 | 9/2006 |
| WO | 2007040280 | 4/2007 |
| WO | 2007057407 | 5/2007 |
| WO | 2007075459 | 7/2007 |
| WO | 2007101369 | 9/2007 |
| WO | 2007115643 | 10/2007 |
| WO | 2007115644 | 10/2007 |
| WO | 2007115646 | 10/2007 |
| WO | 2007141066 A1 | 12/2007 |
| WO | 2007147500 | 12/2007 |
| WO | 2007149134 | 12/2007 |
| WO | 2005085216 | 1/2008 |
| WO | 2008009360 | 1/2008 |
| WO | 2008066153 | 6/2008 |
| WO | 2008067911 | 6/2008 |
| WO | 2008104503 | 9/2008 |
| WO | 2009002956 | 12/2008 |
| WO | 2009029561 | 3/2009 |
| WO | 2009049851 | 4/2009 |
| WO | 2009158478 | 12/2009 |
| WO | 2010005692 | 1/2010 |
| WO | 2010006713 | 1/2010 |
| WO | 2010069502 | 6/2010 |
| WO | 2010074747 | 7/2010 |
| WO | 2010074751 | 7/2010 |
| WO | 2010126657 | 11/2010 |
| WO | 2010138661 | 12/2010 |
| WO | 2011138450 A2 | 11/2011 |
| WO | 2012061991 | 5/2012 |
| WO | 2012116939 | 9/2012 |
| WO | 2013016270 A1 | 1/2013 |
| WO | 2013178668 | 12/2013 |
| WO | 2013178670 A2 | 12/2013 |
| WO | 2013178671 | 12/2013 |
| WO | 2013178679 | 12/2013 |
| WO | 2013178697 | 12/2013 |
| WO | 2013178700 | 12/2013 |
| WO | 2013178701 | 12/2013 |
| WO | 2014056561 A1 | 4/2014 |
| WO | 2014067663 A1 | 5/2014 |
| WO | 2014170025 | 10/2014 |
| WO | 2015082062 | 6/2015 |
| WO | 2015124302 | 8/2015 |
| WO | 2016023693 | 2/2016 |
| WO | 2016041823 | 3/2016 |

OTHER PUBLICATIONS

Bezard (Lipids 1971;6:630-634).
Dale et al. (J. Sci. Food. Agric. 1955;6:166-170) (Year: 1955).
English Translation of Cited Excerpts of CN103468382A, Dec. 25, 2013. 2 pages.
European Coatings Journal in 2009, vol. 07, pp. 26-28.
Friedrich Vogel: "Kosmetik aus der Sicht des Chemikers", Chemie in Unserer Zeit, No. 5, Jan. 1, 1986, pp. 156-164, XP055109030, DOI: 10.1002/ciuz.19860200504, p. 160.
Hardcopy of http://igf-bingen.de/Croda_produkte.pdf, Dec. 1, 2016. 3 pages.
International Preliminary Report on Patentability for PCT/EP2013/061044, dated Feb. 12, 2014. 7 pages.
International Preliminary Report on Patentability for PCT/EP2014/001723, dated Jun. 8, 2015. 16 pages.
International Preliminary Report on Patentability for PCT/EP2015/000443, dated Jan. 22, 2016. 6 pages.
International Preliminary Report on Patentability for PCT/EP2015/076072, dated May 16, 2017. 5 pages.
International Preliminary Report on Patentability for PCT/EP2016/071750, dated Apr. 10, 2018, 5 pages.
International Search Report for PCT/EP2013/003290, dated Feb 10, 2014. 5 pages.
International Search Report for PCT/EP2013/061044, dated May 15, 2014. 2 pages.
International Search Report for PCT/EP2013/061047, dated May 22, 2014. 3 pages.
International Search Report for PCT/EP2013/061075, dated May 15, 2014. 2 pages.
International Search Report for PCT/EP2013/061076, dated May 15, 2014, 2 pages.
International Search Report for PCT/EP2013/061100, dated Jul. 16, 2014. 4 pages.
International Search Report for PCT/EP2013/061100, dated Jul. 15, 2014. 4 pages.
International Search Report for PCT/EP2014/001722, dated Jan. 5, 2015. 3 pages.
International Search Report for PCT/EP2014/001723, dated Jan. 5, 2015. 3 pages.
International Search Report for PCT/EP2015/000443, dated Jun. 2, 2015. 2 pages.
International Search Report for PCT/EP2015/000871 dated Jul. 15, 2015. 3 pages.
International Search Report for PCT/EP2015/072453, dated Oct. 23, 2015. 2 pages.
International Search Report for PCT/EP2015/076072, dated Feb. 29, 2016. 2 pages.
International Search Report for PCT/EP2016/063433, dated Aug. 24, 2016. 2 pages.
International Search Report for PCT/EP2016/071750, dated Jan. 28, 2017, 3 pages.
International Search Report for PCT/EP2016/074085, dated Jan. 3, 2017, 3 pages.
Lichtenthaler, F.W., "Carbohydrates as Organic Raw Materials," in Ullmann's Encyclopedia of Industrial Chemistry, Wiley-VCH Verlag, 2010. (34 pages).
Palm fatty acid distillate (PFAD) [online] retrieved on May 21, 2018 from: https://www.neste.com/corporate-info/sustainability/sustainable-supply-chain/pfa d-residue-palm-oil-refining-process; 1 page (Year: 2018).

(56) References Cited

OTHER PUBLICATIONS

Plante et al. Castor Oil [online] retrieved on Jan. 13, 2016 from: http://www.dionex.com/en-us/webdocs/110518-PO-UHPLC-Castor-Oil-31May2011-LPN2822 -01.pdf; 5 pages.
PubChem, Methylmeglumine, 2006. (Year: 2006) 9 pages.
Quack, et al., Fette-Seifen-Anstrichmittel 78, 200(1976) 7 pages.
R. Mohammadi, J. Wassink, A. Amirfazli, "Effect of Surfactants on Wetting of Super-Hydrophobic Surfaces", Langmuir, American Chemical Society, (Oct. 1, 2004), vol. 20, No. 22, doi:10.1021/la049268k, ISSN 07437463, pp. 9657-9662, XP055098502.
Smith, J.T. et al., "Micellar Electrokinetic Capillary Chromatography with in Situ Charged Micelles. 1. Evaluation of N-D-Gluco-N-methylalkanamide Surfactants as Anionic Borate Complexes," Anal. Chem. 1994, 66, 1119-1133.
Söderlind, E. et al., "The usefulness of sugar surfactants as solubilizing agents in parenteral formulations," Elsevier, I nternational IJournal of Pharmaceutics 252 (2003) pp. 61-71, Aug. 19, 2002.
Study on Synthesis and Properties of "Green" Surfactants—Glucamine derivates, Zhao Handong, Master Thesis, Southern Yangtze University, pp. 5-6, Jul. 25, 2007.
Synergen OS Innovation Spotlight, Sep. 1, 2013, 5 pages.
Tan et al. (Appl Microbiol Biotechnol. 47:207-211) (Year: 1997).
Tegeler, T. et al., Special Guest Editor Section: Electrically Driven Microseparation Methods for Pesticides and Metabolites: I. Micellar Electrokinetic Capillary Chromatography of Carbamate Insecticides with MEGA-Borate and SDS Surfactants, Journal of AOAC International, vol. 82, No. 6, pp. 1542-1549, Nov. 6, 1999.
The Chemistry of Coconut Oil, accessed online Jul. 12, 2018 (Year: 2018) 5 pages.
V. Bergeron, P. Cooper, C. Fischer. J. Giermanska-Kahn, D. Langevin, and A. Pouchelon, "Polydimethylsiloxane (PDMS)-based antifoams" Colloids and Surfaces A: Physicochemical and Engineering Aspects 122 (1997) 103-120. 18 pages.
Walter, A. ; Suchy, S.E. ; Vinson, P.K., "Solubility properties of the alkylmethylglucamide surfactants", Biochimica et Biophysica Acta (BBA)—Biomembranes, Elsevier, Amsterdam, NL, Amsterdam, NL, (Nov. 2, 1990), vol. 1029, No. 1, doi:10.1016/0005-2736(90)90437-S, ISSN 0005-2736, pp. 67-74, XP023354648.
Zhu, Y-P, et al., "Surface Properties of N-Alkanoyl-N-Methy Glucamines and Related Materials", J. of Surfactants and Detergents, vol. 2, No. 3, Jul. 1, 1999. 6 pages.
"Phase behavior studies of quaternary systems containing N-lauroyl-N-methylglucamide/alcohol/alkane/water", Yang et. al., Journal of Colloid and Interface Science, Academic Press, New York, NY, US, vol. 320, No. 1, Feb. 19, 2008, pp. 283-289 (Year: 2008).
Anan Yaghmur et al., Langmuir, vol. 19, No. 4, pa 1063-1068, Feb. 1, 2003.
Bouton et al, Langmuir, vol. 26, No. 11, pp. 7962-7966, Jun. 1, 2010.
Eliana Areanas et al: Langmuir, vol. 12, No. 2, pp. 588-590, Jan. 1, 1996.
Gregory J. McFann et al, Langmuir, vol. 9, No. 11, pp. 2942-2948, Nov. 1, 1993.
Howard, et al., "Comparison of Flowback Aids: Understanding Their Capillary Pressure and Wetting Properties", SPE Paper 122307, 2009, 16 pages.
International Preliminary Report on Patentability for PCT/EP2015/070567, dated Dec. 23, 2016, 12 pages.
International Search Report for PCT/EP2015/070567, dated Mar. 22, 2016, 5 pages.
Panga, et al., "Wettability Alteration for Water-Block Prevention in High-Prevention in High-Temperature Gas Wells", SPE Paper 100182, 2006, 13 pages.
Penny, et al., "Field Studies of Drilling and Completion Fluids to Minimize Damage and Enhance Gas Production in Unconventional Reservoirs", SPE Paper 107844, 2007, 11 pages.
Pursley, et al., "Microemulsion Additive Enable Optimized Formation Damage Repair and Prevention" Paper 86556, 2004, SPE, 7 pages.
Quintero, et al., "Proper Design Criteria of Microemulsion Treatment fluids for Enhancing Well Production", SPE 144451, 2012, 10 pages.
Rickman, et al., "Optimizing Microemulsion/surfactant Packages for Shale and Tight-Gas Reservoirs", Paper 131107, 2010, SPE, 7 pages.
S. Ezrahi et al., Journal of Colloid and Interface Science, vol. 191, No. 2, pp. 277-290, Jul. 1, 1997.
S. Ray et al., Langmuir, vol. 10, No. 8, pp. 2511-2515, Aug. 1, 1994.

\* cited by examiner

COMPOSITIONS COMPRISING SUGAR AMINE AND FATTY ACID

The invention relates to compositions comprising one or more sugar amines and/or protonated sugar amines with fatty acid anions as counterions and one or more fatty acids and/or fatty acid salts, to the use of such compositions for producing liquid detergents or shower baths, liquid soaps or face cleansers, and to the use of the sugar amines as neutralizing agents for fatty acids. The invention furthermore relates to salts of sugar amines and fatty acids.

The use of sugar amines in detergents and cosmetics is already known from the prior art.

DE 42 38 211 C1 describes detergent mixtures comprising specific cationic sugar surfactants, for example derived from glucamines, and the use thereof for producing e.g. detergents and products for hair care and body care. The detergent mixtures are characterized inter alia by a high cold water solubility or cold water dispersibility and can be processed without problems to give highly concentrated, low viscosity solutions or dispersions.

DE 198 08 824 C1 discloses hair treatment compositions with a content of at least one polymer with acidic groups, such as e.g. carboxylic acid groups, and at least one N-unsubstituted or N-substituted polyhydroxyamine with at least four hydroxyl groups, such as e.g. glucamine, and moreover the use of at least one N-unsubstituted or N-substituted polyhydroxyamine with at least four hydroxyl groups in hair treatment compositions for the neutralization of polymers with acidic groups.

EP 1 676 831 A1 describes polyhydroxyalkylamines disubstituted on the nitrogen, such as e.g. N,N-dialkylglucamines, where both substituents each contain 2 to 30 carbon atoms. Furthermore, a large number of application possibilities for the polyhydroxyalkylamines disubstituted on the nitrogen is also disclosed, such as e.g. the use in aqueous liquid detergents or in shampoos, liquid body cleansing formulations, hair conditioning formulations and aqueous sunscreen formulations.

EP 1 529 832 A1 discloses metal working fluids comprising aminopolyols such as, for example, D-glucamine, methylglucamine, ethylglucamine or hydroxyethylglucamine. Moreover, it is described for example that aminopolyols and preferably amino sugars can be used e.g. as neutralizing and reaction component in coating compositions, cosmetics, physiological solutions and carrier substances for medicaments.

EP 614 881 describes the preparation of tertiary dialkylpolyhydroxyamines, such as e.g. dimethylglucamine.

Fatty acids and salts thereof (where the salts of the fatty acids are also referred to as "fatty acid soaps") are highly valuable ingredients of detergents and cleaners. However, typical soap solutions are only homogeneous at a relatively high pH and are often relatively viscous and have inadequate solubility specifically at tendentially lower pH values.

It was therefore the object to provide novel compositions which produce low viscosity, homogeneous solutions of fatty acids or fatty acid soaps in aqueous compositions over a broad pH range and thus facilitate the incorporation of longer-chain fatty acids and/or fatty acid soaps in detergents and cleaners.

Surprisingly, it has now been found that this object is achieved by compositions comprising a) one or more substances selected from the group consisting of sugar amines of the formula (I), protonated sugar amines of the formula (Ia) and mixtures thereof

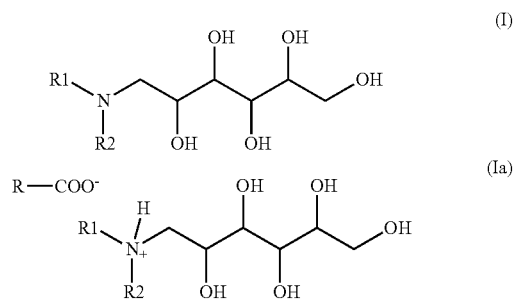

in which

R1 and R2, independently of one another, are H, $CH_3$ or 2-hydroxyethyl and

R has the meaning of R from the substances of component b) below and b) one or more substances selected from the group consisting of fatty acids of the formula R—COOH, fatty acid salts of the formula R—COO⁻M⁺ and mixtures thereof, in which R is a linear or branched saturated alkyl radical having 11 to 21 carbon atoms or a linear or branched mono- or polyunsaturated alkenyl radical having 11 to 21 carbon atoms and M⁺ is a counterion, preferably selected from the group consisting of $NH_4^+$, organic ammonium ions $[HNR^5R^6R^7]^+$, where $R^5$, $R^6$ and $R^7$, independently of one another, can be a linear or branched saturated alkyl group having 1 to 22 carbon atoms, a linear or branched, mono- or polyunsaturated alkenyl group having 2 to 22 carbon atoms, a $C_6$-$C_{22}$-alkylamidopropyl group, a linear monohydroxyalkyl group having 2 to 10 carbon atoms or a linear or branched dihydroxyalkyl group having 3 to 10 carbon atoms, and where at least one of the radicals $R^5$, $R^6$ and $R^7$ is not hydrogen, Li⁺, Na⁺, K⁺, ½Ca⁺⁺, ½Mg⁺⁺, ½Zn⁺⁺ or ⅓Al⁺⁺⁺ and mixtures of these ions.

The invention therefore provides compositions comprising a) one or more substances selected from the group consisting of sugar amines of the formula (I), protonated sugar amines of the formula (Ia) and mixtures thereof

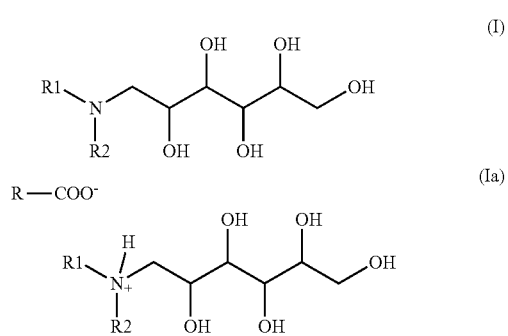

in which

R1 and R2, independently of one another, are H, $CH_3$ or 2-hydroxyethyl and

R has the meaning of R from the substances of component b) below and b) one or more substances selected from the group consisting of fatty acids of the formula R—COOH, fatty acid salts of the formula R—COO⁻M⁺ and mixtures thereof, in which R is a linear or branched saturated alkyl radical having 11 to 21 carbon atoms or a linear or branched mono- or polyunsaturated alkenyl radical having 11 to 21 carbon atoms and M⁺ is a counterion, preferably selected from the group consisting of $NH_4^+$, organic ammonium ions $[HNR^5R^6R^7]^+$, where $R^5$, $R^6$ and $R^7$, independently of one another, can be a linear or branched saturated alkyl group having 1 to 22 carbon atoms, a linear or branched, mono- or polyunsaturated alkenyl group having 2 to 22 carbon atoms, a $C_6$-$C_{22}$-alkylamidopropyl group, a linear monohydroxyalkyl group having 2 to 10 carbon atoms or a linear or branched dihydroxyalkyl group having 3 to 10 carbon atoms, and where at least one of the radicals $R^5$, $R^6$ and $R^7$ is not hydrogen, Li⁺, Na⁺, K⁺, ½Ca⁺⁺, ½Mg⁺⁺, ½Zn⁺⁺ or ⅓Al⁺⁺⁺ and mixtures of these ions.

As already mentioned, the compositions according to the invention have the advantage for example that they produce homogeneous solutions of fatty acids or fatty acid salts in aqueous compositions that are of low viscosity over a broad pH range.

In the compositions according to the invention, the radical R in the protonated sugar amines of the formula (Ia) has the meaning of R from the substances of component b) of the compositions according to the invention. This means that the radical R in the protonated sugar amines of the formula (Ia) also then assumes the meaning of R from the substances of the component b) of the compositions according to the invention if R in the substances of component b) of the compositions according to the invention assumes preferred, particularly preferred, especially preferred meanings etc.

Preferably, the one or more substances of component a) of the compositions according to the invention is or are selected from the group consisting of dimethylglucamine, hydroxyethylmethylglucamine, dimethylglucammonium with the counterion R—COO⁻, hydroxyethylmethylglucammonium with the counterion R—COO⁻ and mixtures thereof.

Dimethylglucammonium with the counterion R—COO⁻ is compounds of the formula (Ia) from component a) of the compositions according to the invention in which R1 and R2 are $CH_3$.

Hydroxyethylmethylglucammonium with the counterion R—COO⁻ is compounds of the formula (Ia) from component a) of the compositions according to the invention in which one of the radicals R1 and R2 is $CH_3$ and the other of these radicals is —$CH_2CH_2$—OH.

Particularly preferably, the one or more substances of component a) is or are selected from the group consisting of dimethylglucamine, dimethylglucammonium with the counterion R—COO⁻ and mixtures thereof.

Preferably, the counterion M⁺ of the fatty acid salts of the formula R—COO⁻M⁺ from component b) of the compositions according to the invention is selected from the group consisting of $NH_4^+$, monoethanolammonium, diethanolammonium, triethanolammonium, methylpropanolammonium, Na⁺, K⁺ and mixtures of these ions and particularly preferably selected from the group consisting of Na⁺, K⁺ and mixtures of these ions.

Preferably, the one or more substances of component b) of the compositions according to the invention is or are selected from the group consisting of the fatty acids (R—COOH) lauric acid, myristic acid, palmitic acid, stearic acid, oleic acid, linolic acid, $C_{16}$/$C_{18}$ fatty acids, behenic acid and erucic acid, the salts of the specified fatty acids with M⁺ as counterion (R—COO⁻M⁺) and mixtures thereof. The preferred embodiment of the invention just described is referred to hereinbelow as "embodiment A".

Particularly preferably, the one or more substances of component b) of the compositions according to the invention is or are selected from the group consisting of $C_{16}$/$C_{18}$ fatty acids, the salts of $C_{16}$/$C_{18}$ fatty acids with M⁺ as counterion and mixtures thereof. The particularly preferred embodiment of the invention just described is referred to hereinbelow as "embodiment B".

Especially preferably, the one or more substances of component b) of the compositions according to the invention is or are selected from the group consisting of oleic acid, the salts of oleic acid with M⁺ as counterion and mixtures thereof. The especially preferred embodiment of the invention just described is referred to hereinbelow as "embodiment C".

In an extraordinarily preferred embodiment of the invention, the one or more substances of component a) of the compositions according to the invention is or are selected from the group consisting of dimethylglucamine, dimethylglucammonium with the counterion R—COO⁻, in which R—COO⁻ corresponds to the oleic acid anion (or deprotonated oleic acid), and mixtures thereof, and the one or more substances of component b) of the compositions according to the invention is or are selected from the group consisting of oleic acid, the salts of oleic acid with M⁺ as counterion and mixtures thereof. The extraordinarily preferred embodiment of the invention just described is referred to hereinbelow as "embodiment D".

In the embodiments A, B, C and D, M⁺ is a counterion, it preferably being selected from the group consisting of $NH_4^+$, organic ammonium ions $[HNR^5R^6R^7]^+$, where $R^5$, $R^6$ and $R^7$, independently of one another, can be hydrogen, a linear or branched saturated alkyl group having 1 to 22 carbon atoms, a linear or branched, mono- or polyunsaturated alkenyl group having 2 to 22 carbon atoms, a $C_6$-$C_{22}$-alkylamidopropyl group, a linear monohydroxyalkyl group having 2 to 10 carbon atoms or a linear or branched dihydroxyalkyl group having 3 to 10 carbon atoms, and where at least one of the radicals $R^5$, $R^6$ and $R^7$ is not hydrogen, Li⁺, Na⁺, K⁺, ½Ca⁺⁺, ½Mg⁺⁺, ½Zn⁺⁺ or ⅓Al⁺⁺⁺ and mixtures of these ions, it being particularly preferably selected from the group consisting of $NH_4^+$, monoethanolammonium, diethanolammonium, triethanolammonium, methylpropanolammonium, Na⁺, K⁺ and mixtures of these ions and it being especially preferably selected from the group consisting of Na⁺, K⁺ and mixtures of these ions.

Among the compositions according to the invention, preference is given to those in which component a) comprises one or more protonated sugar amines of the formula (Ia). In these preferred compositions according to the invention, the sugar amines of the formula (I) from component a) are only optionally present.

Among the compositions according to the invention, in a preferred embodiment of the invention, preference is given to those in which component b) comprises one or more fatty acids of the formula R—COOH. In these preferred compositions according to the invention, the fatty acid salts of the formula R—COO⁻M⁺ from component b) are only optionally present. Among these preferred compositions according to the invention, in a particularly preferred embodiment of the invention, preference is in turn given to those in which component b) comprises no fatty acid salts of the formula R—COO⁻M⁺.

Preferably, the compositions according to the invention comprise water.

The substances of the formula (Ia) from component a) and the substances of component b) of the compositions according to the invention are surfactants. In this connection, not only are the substances of the formula (Ia) and the fatty acid salts of the formula R—COO⁻M⁺ from component b) of the compositions according to the invention anionic surfactants, but in the context of the present invention the fatty acids R—COOH of component b) of the compositions according to the invention are also considered to be anionic surfactants. By contrast, the substances of the formula (I) from component a) of the compositions according to the invention are not surfactants.

Besides the substances of the formula (Ia) from component a) and the substances of component b), the compositions according to the invention preferably comprise one or more further surfactants.

In the context of the present invention, such further surfactants are referred to as substances which reduce the surface tension of a liquid or the interfacial tension between two phases and facilitate or assist the formation of dispersions or emulsions. This means in particular that the term "surfactants" in the context of the present invention also include substances which are usually referred to as emulsifiers.

The further surfactants can advantageously be selected from the group consisting of nonionic surfactants, anionic surfactants, cationic surfactants, amphoteric surfactants and betaine surfactants.

The amount of surfactants present in the compositions according to the invention (including the substances of component b) and the substances of the formula (Ia) from component a) of the compositions according to the invention) is, based on the total weight of the compositions according to the invention, preferably from 0.01 to 60.0% by weight, particularly preferably from 1.0 to 40.0% by weight, especially preferably from 2.0 to 30.0% by weight and extraordinarily preferably from 3.0 to 15.0% by weight.

As further anionic surfactants, preference is given to $(C_{10}-C_{22})$-alkyl ethercarboxylates, fatty alcohol sulfates such as e.g. lauryl sulfate, fatty alcohol ether sulfates such as e.g. lauryl ether sulfate (or laureth sulfate), alkylamidosulfates, alkylamidosulfonates, fatty acid alkylamide polyglycol ether sulfates, alkanesulfonates, hydroxyalkanesulfonates, olefinsulfonates, acyl esters of isethionates, α-sulfo fatty acid esters (methyl ester sulfonates), alkylbenzenesulfonates, preferably linear alkylbenzenesulfonates, alkylphenol glycol ether sulfonates, sulfosuccinates, sulfosuccinic acid half-esters, sulfosuccinic acid diesters, fatty alcohol phosphates, fatty alcohol ether phosphates, protein-fatty acid condensation products, alkyl monoglyceride sulfates, alkyl monoglyceride sulfonates, alkyl glyceride ether sulfonates, fatty acid methyltaurides, fatty acid sarcosinates, sulforicinoleates, acyl glutamates such as e.g. sodium cocoylglutamate and acyl glycinates. These compounds and mixtures thereof are used in the form of their water-soluble or water-dispersible salts, for example in the form of their sodium salts, potassium salts, magnesium salts, ammonium salts, monoethanolammonium salts, diethanolammonium salts and/or triethanolammonium salts, and the analogous alkylammonium salts.

The amount of anionic surfactants in the compositions according to the invention (including the substances of component b) and the substances of the formula (Ia) from component a) of the compositions according to the invention) is, based on the total weight of the compositions according to the invention, preferably from 0.1 to 30.0% by weight, particularly preferably from 0.2 to 20.0% by weight and especially preferably from 0.5 to 15.0% by weight.

Preferred cationic surfactants are quaternary ammonium salts such as di-$(C_8-C_{22})$-alkyl-dimethylammonium chloride or bromide;

$(C_8-C_{22})$-alkyldimethylethylammonium chloride or bromide;

$(C_8-C_{22})$-alkyltrimethylammonium chloride or bromide, preferably cetyltrimethylammonium chloride or bromide;

$(C_{10}-C_{24})$-alkyldimethylbenzylammonium chloride or bromide, preferably $(C_{12}-C_{10})$-alkyldimethylbenzylammonium chloride;

$(C_8-C_{22})$-alkyldimethylhydroxyethylammonium chloride, phosphate, sulfate or lactate;

$(C_8-C_{22})$-alkylamidopropyltrimethylammonium chloride or methosulfate;

N,N-bis(2-$C_8-C_{22}$-alkanoyloxyethyl)dimethylammonium chloride or methosulfate, and N,N-bis(2-$C_8-C_{22}$-alkanoyloxyethyl)hydroxyethylmethylammonium chloride or methosulfate.

The amount of cationic surfactants in the compositions according to the invention is, based on the total weight of the compositions according to the invention, preferably from 0.1 to 10.0% by weight, particularly preferably from 0.5 to 7.0% by weight and especially preferably from 1.0 to 5.0% by weight.

As nonionic surfactants, preference is given to fatty alcohol ethoxylates (alkyl polyethylene glycols); alkylphenol polyethylene glycols; fatty amine ethoxylates (alkylaminopolyethylene glycols); fatty acid ethoxylates (acylpolyethylene glycols); polypropylene glycol ethoxylates (Pluronics®); fatty acid alkanolamides, (fatty acid amide polyethylene glycols); N-acyl-N-methylglucamines; sucrose esters; sorbitol esters and sorbitan esters and the polyglycol ethers thereof; $C_8-C_{22}$-alkyl polyglucosides.

The amount of nonionic surfactants in the compositions according to the invention is, based on the total weight of the compositions according to the invention, preferably from 1.0 to 20.0% by weight, particularly preferably from 2.0 to 10.0% by weight and especially preferably from 3.0 to 7.0% by weight.

Furthermore, the compositions according to the invention can comprise amphoteric surfactants. These can be described as derivatives of long-chain secondary or tertiary amines which have an alkyl group with 8 to 18 carbon atoms and in which a further group is substituted with an anionic group which imparts solubility in water, thus e.g. with a carboxyl group, sulfate group or sulfonate group. Preferred amphoteric surfactants are aminopropionates such as N—$(C_{12}-C_{18})$-alkyl-β-aminopropionates and N—$(C_{12}-C_{18})$-alkyl-β-iminodipropionates as alkali metal salts, monoalkylammonium salts, dialkylammonium salts or trialkylammonium salts, and lauroamphoacetate, in particular as sodium salt.

Suitable further surfactants are also amine oxides. These are oxides of tertiary amines with a long-chain group of 8 to 18 carbon atoms and two mostly short-chain alkyl groups having 1 to 4 carbon atoms. Preference is given here, for example, to the $C_{10}$- to $C_{18}$-alkyldimethylamine oxides and fatty acid amidoalkyldimethylamine oxides.

A further preferred group of surfactants are betaine surfactants, also called zwitterionic surfactants. These contain a cationic group, in particular an ammonium group, and an anionic group, which can be a carboxylate group, sulfate group or sulfonate group, in the same molecule. Suitable betaines are preferably alkylbetaines such as cocobetaine or fatty acid alkylamidopropylbetaines (or alkylamidopropylbetaines), for example cocoacylamidopropyldimethylbetaine (or cocoamidopropylbetaine).

The amount of amphoteric surfactants and/or betaine surfactants in the compositions according to the invention is, based on the total weight of the compositions according to the invention, preferably from 0.5 to 20.0% by weight and particularly preferably from 1.0 to 15.0% by weight.

In a preferred embodiment of the invention, the compositions according to the invention comprise one or more surfactants selected from the group consisting of lauryl sulfate, laureth sulfate, methyl ester sulfonate, cocoamidopropylbetaine, alkylbetaines such as cocobetaine, sodium cocoyl glutamate and lauroamphoacetate.

In a further preferred embodiment of the invention, the compositions according to the invention comprise one or more surfactants selected from the group consisting of alkylated ether sulfates with a linear or branched alkyl group having 8 to 30 carbon atoms or a linear or branched mono- or polysaturated alkenyl group having 8 to 30 carbon atoms, betaines and derivatives thereof, and mixtures thereof and especially preferably selected from the group consisting of alkylated ether sulfates with a linear or branched alkyl group having 12 to 22 carbon atoms, betaines and derivatives thereof, and mixtures thereof.

In a further preferred embodiment the compositions according to the invention comprise one or more further anionic surfactants besides the substances of the formula (Ia) from component a) and the substances of component b). Among these, the one or more further anionic surfactants is or are in turn preferably selected from the group consisting of alkyl or alkenyl polyglycol ether sulfate, preferably alkyl polyglycol ether sulfate, alkyl or alkenyl sulfate, preferably alkyl sulfate, methyl ester sulfonate, alkylbenzenesulfonate, acyl glutamate and mixtures thereof. In the one or more further anionic surfactants just mentioned, "alkyl" is preferably a linear or branched saturated alkyl group having 12 to 22 carbon atoms, "alkenyl" is a linear or branched mono- or polyunsaturated alkenyl group having 12 to 22 carbon atoms and "acyl" is a linear or branched saturated acyl group having 12 to 22 carbon atoms or a linear or branched mono- or polyunsaturated acyl group having 12 to 22 carbon atoms.

In a further preferred embodiment of the invention, the compositions according to the invention comprise one or more nonionic surfactants selected from the group consisting of alkyl or alkenyl ethoxylates, preferably alkyl ethoxylates, alkyl polyglucosides, acyl-N-methylglucamines, fatty acid alkanolamides such as, for example, coconut fatty acid monoethanolamide and mixtures thereof. In the one or more nonionic surfactants just mentioned, "alkyl" is preferably a linear or branched saturated alkyl group having 12 to 22 carbon atoms, "alkenyl" is a linear or branched mono- or polyunsaturated alkenyl group having 12 to 22 carbon atoms and "acyl" is a linear or branched saturated acyl group having 12 to 22 carbon atoms or a linear or branched mono- or polyunsaturated acyl group having 12 to 22 carbon atoms. The fatty acid groups preferably have acyl groups as just defined for "acyl".

Preferably, the compositions according to the invention comprise, based on the total weight of the compositions according to the invention, 0.5 to 30% by weight, particularly preferably 0.5 to 20% by weight, especially preferably 1 to 15% by weight and extraordinarily preferably 1 to 10% by weight, of the one or more substances of component a).

Preferably, the compositions according to the invention comprise, based on the total weight of the compositions according to the invention, 0.5 to 30% by weight and particularly preferably 1 to 10% by weight of the one or more substances of component b).

Preferably, the molar ratio of component (i): component (ii) in the compositions according to the invention is from 5:1 to 1:5 and particularly preferably from 3:1 to 1:3, where in this connection component (i) consists of the one or more substances of component b) of the compositions according to the invention and the one or more anions RCOO⁻ of the one or more protonated sugar amines of the formula (Ia) from component a) of the compositions according to the invention, and component (ii) consists of the one or more sugar amines of the formula (I) from component a) of the compositions according to the invention and the one or more cations of the protonated sugar amines of the formula (Ia) from component a) of the compositions according to the invention.

In a particularly preferred embodiment of the invention, the molar ratio of component (i): component (ii) in the compositions according to the invention is from 5:1 to 1:1 and particularly preferably from 3:1 to 1:1, where in this connection component (i) consists of the one or more substances of component b) of the compositions according to the invention and the one or more anions RCOO⁻ of the one or more protonated sugar amines of the formula (Ia) from component a) of the compositions according to the invention, and component (ii) consists of the one or more sugar amines of the formula (I) from component a) of the compositions according to the invention and the one or more cations of the protonated sugar amines of the formula (Ia) from component a) of the compositions according to the invention.

In a further particularly preferred embodiment of the invention, the molar ratio of component (i): component (ii) in the compositions according to the invention is from 1:1 to 1:5 and especially preferably from 1:1 to 1:3, where in this connection component (i) consists of the one or more substances of component b) of the compositions according to the invention and the one or more anions RCOO⁻ of the one or more protonated sugar amines of the formula (Ia) from component a) of the compositions according to the invention, and component (ii) consists of the one or more sugar amines of the formula (I) from component a) of the compositions according to the invention and the one or more cations of the protonated sugar amines of the formula (Ia) from component a) of the compositions according to the invention.

Preferably, the compositions according to the invention have a pH of 7 to 11 and particularly preferably from 8 to 10.

The pH values of the compositions according to the invention are measured directly in the compositions using a Knick Portamess 911 single-rod measurement electrode after calibration with corresponding standard buffers. Calibration is performed at pH 4 with citric acid/sodium hydroxide solution/hydrochloric acid buffer and at pH 7 with disodium hydrogenphosphate, potassium dihydrogenphosphate buffer.

Preferably, the compositions according to the invention have a viscosity <500 mPas and particularly preferably <100 mPas.

The viscosities are measured using a Brookfield viscometer model DV II, the spindles from the spindle set RV at 20 revolutions/minute and 20° C. Spindles 1 to 7 from the spindle set RV are used. Under these measurement conditions, spindle 1 is selected for viscosities of at most 500 mPa·s, spindle 2 is selected for viscosities of at most 1000 mPa·s, spindle 3 for viscosities of at most 5000 mPa·s, spindle 4 for viscosities of at most 10 000 mPa·s, spindle 5 for viscosities of at most 20 000 mPa·s, spindle 6 for viscosities of at most 50 000 mPa·s and spindle 7 for viscosities of at most 200 000 mPa·s.

In a preferred embodiment of the invention, the compositions according to the invention are in the form of a liquid detergent and particularly preferably in the form of a highly concentrated liquid detergent.

In a further preferred embodiment of the invention, the compositions according to the invention are in the form of a shower bath, a liquid soap or a face cleanser.

Instead of compositions which are directly suitable for an end use, the compositions according to the invention can also be in the form of concentrates that can be used in particular for producing compositions for certain end uses. The concentrates just mentioned are referred to hereinbelow as "concentrates according to the invention". Preferably, the amount of the one or more substances of component a) in the concentrates according to the invention, based on the total weight of the concentrates according to the invention, is from 10 to 40% by weight. Furthermore, the amount of the one or more substances of component b) in the concentrates according to the invention, based on the total weight of the concentrates according to the invention, is from 5 to 40% by weight.

The compositions according to the invention, in particular the concentrates according to the invention, are advantageously suitable for producing liquid detergents and preferably highly concentrated liquid detergents. The present invention therefore further provides the use of a composition according to the invention, in particular of a concentrate according to the invention, for producing liquid detergents and preferably highly concentrated liquid detergents.

The compositions according to the invention, in particular the concentrates according to the invention, are furthermore advantageously suitable for producing shower baths, liquid soaps or face cleansers. The present invention therefore further provides the use of a composition according to the invention, in particular of a concentrate according to the invention, for producing shower baths, liquid soaps or face cleansers.

Furthermore, the sugar amines of the formula (I) present in component a) of the compositions according to the invention are advantageously suitable as neutralizing agents for fatty acids and preferably for the fatty acids present in component b) of the compositions according to the invention. The present invention therefore also further provides the use of one or more sugar amines of the formula (I)

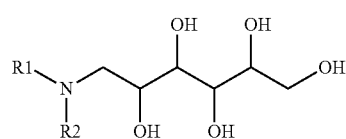
(I)

in which R1 and R2, independently of one another, are H, CH$_3$ or 2-hydroxyethyl, as neutralizing agents for fatty acids and preferably for one or more fatty acids of the formula R—COOH in which R is a linear or branched saturated alkyl radical having 11 to 21 carbon atoms or a linear or branched mono- or polyunsaturated alkenyl radical having 11 to 21 carbon atoms.

In the case of the use according to the invention as neutralizing agent, the one or more sugar amines of the formula (I) is or are preferably selected from the group consisting of dimethylglucamine, hydroxyethylmethylglucamine and mixtures thereof.

In the case of the use according to the invention as neutralizing agent, the sugar amine of the formula (I) is particularly preferably dimethylglucamine.

In the case of the use according to the invention as neutralizing agent, the one or more fatty acids of the formula R—COOH is or are preferably selected from the group consisting of lauric acid, myristic acid, palmitic acid, stearic acid, oleic acid, linolic acid, $C_{16}/C_{18}$ fatty acids, behenic acid, erucic acid and mixtures thereof.

In the case of the use according to the invention as neutralizing agent, the one or more fatty acids of the formula R—COOH is or are particularly preferably selected from the group consisting of $C_{16}/C_{18}$ fatty acids and mixtures thereof.

In the case of the use according to the invention as neutralizing agent, the fatty acid of the formula R—COOH is particularly preferably oleic acid.

In an extraordinarily preferred embodiment of the use according to the invention as neutralizing agent, the sugar amine of the formula (I) is dimethylglucamine and the fatty acid of the formula R—COOH is oleic acid.

In the case of the use according to the invention as neutralizing agent, the molar ratio of the one or more fatty acids of the formula R—COOH to the one or more sugar amines of the formula (I) is preferably from 5:1 to 1:5 and particularly preferably from 3:1 to 1:3.

The present invention also further provides the salts of the formula (Ia) as described for the compositions according to the invention.

The salts according to the invention are advantageously suitable as surfactants. Moreover, they have the advantage for example that they dissolve very readily in water.

The salts according to the invention are in particular the salts of the formula (Ia)

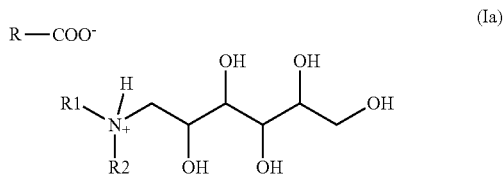
(Ia)

in which

R1 and R2, independently of one another, are H, CH$_3$ or 2-hydroxyethyl and

R is a linear or branched saturated alkyl radical having 11 to 21 carbon atoms or a linear or branched mono- or polyunsaturated alkenyl radical having 11 to 21 carbon atoms.

The salts of the formula (Ia) according to the invention are preferably selected from the group consisting of dimethylglucammonium with the counterion R—COO$^-$, hydroxyethylmethylglucammonium with the counterion R—COO$^-$ and mixtures thereof.

Particularly preferably, the salts of the formula (Ia) according to the invention are selected from the group consisting of dimethylglucammonium with the counterion R—COO⁻ and mixtures thereof.

Preferably, the counterion R—COO⁻ in the salts of the formula (Ia) according to the invention is selected from the group consisting of the fatty acids lauric acid, myristic acid, palmitic acid, stearic acid, oleic acid, linolic acid, $C_{16}/C_{18}$ fatty acids, behenic acid and erucic acid, in each case in deprotonated form, and mixtures thereof.

Particularly preferably, the counterion R—COO⁻ in the salts of the formula (Ia) according to the invention is selected from the group consisting of $C_{16}/C_{18}$ fatty acids, in each case in deprotonated form, and mixtures thereof.

Particularly preferably, the counterion R—COO⁻ in the salts of the formula (Ia) according to the invention is oleic acid in deprotonated form.

Extraordinarily preferably, the salt of the formula (Ia) according to the invention is dimethylglucammonium with deprotonated oleic acid as counterion R—COO⁻.

The invention is illustrated in more detail below by reference to examples, although these should not be interpreted as limiting. Unless explicitly stated otherwise, all percentages are percentages by weight (% by weight).

The dimethylglucamine used in the examples was obtained according to EP 614 881 from N-methylglucamine by reductive amination.

EXAMPLE 1

5 g of oleic acid were introduced into 95 g of water (two-phase) and admixed with increasing molar amounts of different neutralizing agents up to 100 mol % of neutralizing agent. During this, the viscosity was determined (Brookfield, 20° C., 20 revolutions per minute (rpm), spindle 1 or 2), the homogeneity of the resulting solution was observed and the pH was measured (see table 1).

The following values are listed in table 1 and the following abbreviations were used therein:

The upper number in the respective lines of table 1 gives the measured viscosity in mPa·s.

"T" means: the solution is two-phase.

"C" means: the solution is clear.

"H" means: the solution is homogeneous, but cloudy.

The lower number in the respective lines of table 1 gives the measured pH. Here, "n.d." means not determined.

It can be seen from the values in table 1 that in the case of neutralization of oleic acid with dimethylglucamine, low viscosity, homogeneous solutions result even at low degrees of neutralization. Homogeneous solutions are already obtained above a pH of 8.0.

FORMULATION EXAMPLES

Formulation Example 1

Highly Concentrated Liquid Detergent ("Heavy Duty Liquid")

| Ingredient | Amount [% by weight] |
|---|---|
| Methyl ester sulfonate | 6 |
| Linear alkylbenzenesulfonate | 3 |
| Sodium lauryl ether sulfate (2 EO) | 11 |
| Fatty acid (30% by weight $C_{12}$, 25% by weight $C_{14}$, 20% by weight $C_{16}$, 25% by weight $C_{18}$ unsaturated) | 3 |
| $C_{12}/C_{15}$ alkyl ethoxylate (8 EO) | 15 |
| Water | 51.5 |
| Propylene glycol | 2 |
| Dimethylglucamine | 2 |
| Enzymes | 0.7 |
| Polycarboxylate | 0.6 |
| Sodium citrate | 5 |
| Borax | 0.2 |
| Sodium hydroxide | to pH 7.7 |

TABLE 1 neutralizing agents used and also viscosity, homogeneity and pH of prepared compositions

| Neutralizing agent [mol %] | 10 | 20 | 30 | 40 | 50 | 60 | 70 | 80 | 90 | 100 |
|---|---|---|---|---|---|---|---|---|---|---|
| Monoethanol- amine (comparison) | 10<br>T<br>7.3 | 8<br>T<br>7.7 | 8<br>T<br>7.7 | 625<br>H<br>7.7 | 1060<br>H<br>7.7 | 870<br>H<br>8.7 | 540<br>H<br>8.7 | 28<br>H<br>9.2 | 600<br>H<br>9.3 | 825<br>H<br>9.5 |
| Triethanolamine (comparison) | 4<br>T<br>n.d. | 6<br>T<br>n.d. | 104<br>T<br>n.d. | 1440<br>H<br>n.d. | 1220<br>H<br>n.d. | 980<br>H<br>n.d. | 910<br>H<br>n.d. | 750<br>H<br>n.d. | 470<br>H<br>n.d. | 420<br>H<br>n.d. |
| Aminomethyl- propanol (comparison) | 6<br>T<br>n.d. | 6<br>T<br>n.d. | 9<br>T<br>n.d. | 560<br>H<br>n.d. | 535<br>H<br>n.d. | 183<br>H<br>n.d. | 70<br>H<br>n.d. | 160<br>H<br>n.d. | 2860<br>H<br>n.d. | 4200<br>C<br>n.d. |
| Sodium hydroxide solution (comparison) | 6<br>T<br>8.3 | 6<br>T<br>8.3 | 8<br>T<br>8.2 | 13<br>T<br>8.5 | 38<br>H<br>8.6 | 23<br>H<br>9.2 | 13<br>H<br>9.6 | 9<br>T<br>9.7 | 6<br>T<br>9.7 | 6<br>C<br>11.3 |
| Dimethyl- glucamine (invention) | 5<br>T<br>7.1 | 15<br>H<br>8.0 | 25<br>H<br>8.1 | 70<br>H<br>8.1 | 30<br>H<br>8.5 | 20<br>H<br>8.9 | 20<br>H<br>8.8 | 10<br>H<br>8.9 | 10<br>H<br>8.8 | 10<br>C<br>8.8 |

Formulation Example 2

Highly Concentrated Liquid Detergent ("Heavy Duty Liquid")

| Ingredient | Amount [% by weight] |
| --- | --- |
| Linear alkylbenzene-sulfonate | 8 |
| Sodium lauryl ether sulfate (2 EO) | 9 |
| Fatty acid (30% by weight $C_{12}$, 20% by weight $C_{14}$, 15% by weight $C_{16}$, 5% by weight $C_{18}$ saturated, 30% by weight $C_{18}$ unsaturated) | 5 |
| $C_{12}/C_{14}$ alkyl ethoxylate (7 EO) | 8 |
| Water | 48.5 |
| Ethanol | 2 |
| Propylene glycol | 6 |
| Dimethylglucamine | 5 |
| Enzymes | 2 |
| Soil Release Polyester | 0.7 |
| Sodium citrate | 5 |
| Borax | 0.8 |
| Sodium hydroxide to pH 8.5 | |

Formulation Example 3

Highly Concentrated Liquid Detergent in Monodose Format ("Monodose Surfactant Capsule")

| Ingredient | Amount [% by weight] |
| --- | --- |
| Linear alkylbenzene-sulfonate | 24 |
| Fatty acid (30% by weight $C_{12}$, 20% by weight $C_{14}$, 15% by weight $C_{16}$, 5% by weight $C_{18}$ saturated, 30% by weight $C_{18}$ unsaturated) | 23 |
| $C_{10}$ alkyl ethoxylate (10 EO) | 19 |
| Water | 4 |
| Ethanol | 4 |
| Propylene glycol | 10 |
| Dimethylglucamine | 8 |
| Enzymes | 0.7 |
| Complexing agent | 0.5 |
| Methylpropanediol | 6.8 |
| Sodium hydroxide to pH 8.4 | |

Formulation Example 4

Shower Bath/Liquid Soap

| Ingredient | Amount [% by weight] |
| --- | --- |
| Lauric acid | 6 |
| Myristic acid | 4 |
| Palmitic acid | 2 |
| Dimethylglucamine | 5 |
| Sodium cocoylglutamate | 2 |
| Cocamide MEA (coconut fatty acid monoethanolamide) | 3 |
| Hydroxypropylmethylcellulose | 0.2 |
| Water | ad 100 |
| pH with potassium hydroxide solution to pH = 8.6 | |

Formulation Example 5

Face Cleanser

| Ingredient | Amount [% by weight] |
| --- | --- |
| Lauric acid | 6 |
| Myristic acid | 4 |
| Palmitic acid | 2 |
| Dimethylglucamine | 5 |
| Sodium cocoylglutamate | 2 |
| Oleoylmethylglucamide | 3 |
| Hydroxypropylmethylcellulose | 0.2 |
| Water | ad 100 |
| pH with potassium hydroxide solution to pH = 8.5 | |

The invention claimed is:

1. A composition comprising
    a) one or more substances selected from the group consisting of dimethylglucammonium compounds with the counterion R—COO$^-$; hydroxyethylmethyl-glucammonium compounds with the counterion R—COO$^-$; and mixtures thereof,
  wherein
    R is defined in component b) below
  and
    b) one or more substances selected from the group consisting of fatty acids of the formula R—COOH, fatty acid salts of the formula R—COO$^-$M$^+$, and mixtures thereof, in which
    R is a linear or branched saturated alkyl radical having 11 to 21 carbon atoms or a linear or branched mono- or polyunsaturated alkenyl radical having 11 to 21 carbon atoms and
    M$^+$ is a counterion.

2. The composition as claimed in claim 1, wherein the one or more substances of component a) are selected from the group consisting of dimethylglucammonium compounds with the counterion R—COO$^-$, and mixtures thereof.

3. The composition as claimed in claim 1, wherein the counterion M$^+$ is selected from the group consisting of NH$_4^+$, monoethanolammonium, diethanolammonium, triethanolammonium, methylpropanolammonium, Na$^+$, K$^+$ and mixtures of these ions.

4. The composition as claimed in claim 1, wherein the one or more substances of component b) are selected from the group consisting of lauric acid, myristic acid, palmitic acid, stearic acid, oleic acid, linolic acid, $C_{16}/C_{18}$ fatty acids, behenic acid, erucic acid, the salts of the specified fatty acids with $M^+$ as counterion (R—COO$^-$M$^+$) and mixtures thereof.

5. The composition as claimed in claim 1, wherein the one or more substances of component b) are selected from the group consisting of $C_{16}/C_{18}$ fatty acids, the salts of $C_{16}/C_{18}$ fatty acids with $M^+$ as counterion and mixtures thereof.

6. The composition as claimed in claim 1, wherein the one or more substances of component b) are selected from the group consisting of oleic acid, the salts of oleic acid with $M^+$ as counterion and mixtures thereof.

7. The composition as claimed in claim 1, wherein component b) comprises one or more fatty acids of the formula R—COOH and comprises no fatty acid salts of the formula R—COO$^-$M$^+$.

8. The composition as claimed in claim 1, further comprising water.

9. The composition as claimed in claim 1, further comprising one or more anionic surfactants besides the substances of component a) and the substances of component b).

10. The composition as claimed in claim 9, wherein the one or more anionic surfactants are selected from the group consisting of alkyl- or alkenylpolyglycol ether sulfate, alkyl or alkenyl sulfate, methyl ester sulfonate, alkylbenzenesulfonate, acylglutamate and mixtures thereof.

11. The composition as claimed in claim 1, further comprising one or more nonionic surfactants selected from the group consisting of alkyl or alkenyl ethoxylates, alkylpolyglucosides, acyl-N-methylglucamines, fatty acid alkanolamides and mixtures thereof.

12. The composition as claimed in claim 1, wherein it comprises, based on the total weight of the composition, 0.5 to 30% by weight, of the one or more substances of component a).

13. The composition as claimed in claim 1, wherein it comprises, based on the total weight of the composition, 0.5 to 30% by weight of the one or more substances of component b).

14. The composition as claimed in claim 1, wherein the composition has a pH of from 7 to 11.

15. The composition as claimed in claim 1, wherein the composition has a viscosity <500 mPas.

16. A liquid detergent comprising at least one composition as claimed in claim 1.

17. A shower bath, a liquid soap or a face cleanser comprising at least one composition as claimed in claim 1.

18. A method for producing a liquid detergent, comprising the step of adding at least one composition as claimed in claim 1, to a liquid detergent.

19. A method for producing a shower bath, liquid soap or face cleanser comprising the step of adding at least one composition as claimed in claim 1, to the shower bath, liquid soap or face cleanser.

20. The composition as claimed in claim 1, wherein $M^+$ is selected from the group consisting of Li$^+$, Na$^+$, K$^+$, ½ Ca$^{++}$, ½ Mg$^{++}$, ½ Zn$^{++}$, ⅓ Al$^{+++}$, NH$_4^+$, organic ammonium ions [HNR$^5$R$^6$R$^7$]$^+$, where R$^5$, R$^6$ and R$^7$, independently of one another, can be a linear or branched saturated alkyl group having 1 to 22 carbon atoms, a linear or branched, mono- or polyunsaturated alkenyl group having 2 to 22 carbon atoms, a $C_6$-$C_{22}$-alkylamidopropyl group, a linear monohydroxyalkyl group having 2 to 10 carbon atoms or a linear or branched dihydroxyalkyl group having 3 to 10 carbon atoms, and where at least one of the radicals R$^5$, R$^6$ and R$^7$ is not hydrogen, and mixtures thereof.

21. The composition as claimed in claim 1, further comprising one or more substances selected from the group consisting of dimethylglucamine; hydroxyethylmethylglucamine; and mixtures thereof.

* * * * *